US Patent Number: 5,030,634
Date of Patent: Jul. 9, 1991
Krumdieck et al.

[54] 10-DEAZAAMINOPTERIN: A NEW ARTHRITIS REMITTIVE DRUG

[76] Inventors: Carlos L. Krumdieck, 3408 Welford Cir., Birmingham, Ala. 35226; Oswaldo Castaneda, Apartment 2713, Clinica Anglo Americana, Lima, Peru; Graciela Alarcon, 1221 Rumson Dr., Birmingham, Ala. 35226; William J. Koopman, 452-H Wildwood La., Helena, Ala. 35080; Madhavan G. Nair, 7005 Charleston Oaks Dr., Mobile, Ala. 36695

[21] Appl. No.: 500,911

[22] Filed: Mar. 29, 1990

[51] Int. Cl.$^5$ .................. A61K 31/495; A61K 31/50
[52] U.S. Cl. ..................................... 514/249; 514/825
[58] Field of Search ........................ 514/249, 826, 825

[56] References Cited

U.S. PATENT DOCUMENTS

| 4,369,319 | 1/1983 | DeGraw, Jr. et al. | 544/260 |
| 4,393,064 | 7/1983 | DeGraw, Jr. et al. | 424/251 |
| 4,746,659 | 5/1988 | DeGraw et al. | 514/249 |
| 4,889,859 | 12/1989 | Taylor et al. | 514/258 |

OTHER PUBLICATIONS

DeGraw, J. I. et al. Synthesis & antitumor activity of 10-alkyl-10-DeAzaminopterins, A convenient synthesis of 10-Deazaminopterin J. Medicinal Chem., 25(10): 1227–1230 (1982).

DeGraw, Kisliuk, Gaumont, Baugh and Nair J. Med. Chem 17,552.1974.

Nair, J. Org. Chem. 50,1879,1985.

Thongprasert, Currie and Budman Canc. Treat. Rep. 71,995,1987.

Nair, Nanavati, Kumar, Gaumont and Kisliuk. J. Med. Chem. 31,181,1988.

Primary Examiner—Glennon H. Hollrah
Assistant Examiner—Gary E. Hollinden

[57] ABSTRACT

A double blind clinical trial of 10-deazaaminopterin versus the antirheumatoid drug methotrexate (MTX) established that 10-deazaaminopterin, in addition to being at least equally effective as methotrexate in all respects in ameliorating rheumatoid arthritis in humans, it is superior to methotrexate in controlling pain and joint stiffness and in improving grip strength. In accordance with this invention 10-deazaaminopterin is claimed as a more effective disease modifying arthritis remittive drug for the treatment of rheumatoid arthritis in humans.

3 Claims, No Drawings

10-DEAZAAMINOPTERIN: A NEW ARTHRITIS REMITTIVE DRUG

USE ADVANTAGE

Methotrexate is the only effective drug currently available in the classical antifolate series for the treatment of rheumatoid arthritis and related inflammatory diseases such as asthma in humans. Methotrexate is a very toxic drug and the use of methotrexate in rheumatoid arthritis is limited by its toxicity. Many rheumatologists have concluded that toxicity is the major factor limiting prolonged MTX therapy. Toxic manifestations such as nausea, stomatitis, elevated liver function tests, cytopenias, and pulmonary toxicity have generally been reported in 30-60% of patients receiving the drug. A recent two year study documented that 93% of patients experienced an adverse drug reaction during treatment.

10-deazaaminopterin is a more powerful anti-proliferative agent than methotrexate; yet in clinical trials it was found to be remarkably less toxic to humans. In clinical trials as an anti-rheumatoid drug 10-deazaaminopterin was found to be superior to methotrexate. 10-deazaaminopterin used for this study was prepared by the procedure of Nair as described in the *Journal of Organic Chemistry* (50:1875, 1985) as opposed to the more elaborate and expensive procedures using unstable intermediates for the preparation of methotrexate. Therefore, 10-deazaaminopterin can be considered as less toxic, more effective and an inexpensive anti-rheumatoid drug compared to methotrexate.

Rheumatoid arthritis is a chronic systemic disease believed to be of auto-immune origin. Common to all auto-immune diseases is the failure of the body's immune system to distinguish between self and non-self and to attack its own tissues as if belonging to a foreign organism. Severe articular pain and tissue destruction, leading to crippling joint deformities, as well as systemic manifestations such as vasculitis, heart disease, anemia, subcutaneous nodule formation, eye involvement, and others, are characteristic of this disease. There is no cure for rheumatoid arthritis. Drug therapy is aimed at reducing chronic inflammation and pain and at preventing progression of the disease. Aside from anti-inflammatory steroids, two classes of drugs are currently available for the treatment of this disease. One is made up by the non-steroidal anti-inflammatory drugs (NSAIDs) that help control inflammation and alleviate the pain and swelling of affected joints, but that have limited if any effect on the progression of the disease. Examples are aspirin, and a number of newer inhibitors of prostaglandin synthesis such as ibuprofen, naproxen, indomenthacin, fenoprofen, sulindac, meclofenamate, and other related compounds. The second class is referred to as the disease modifying arthritis remittive drugs (DMARDs). Compounds in this class appear to arrest progression of the disease by mechanisms that remain largely unknown. Examples are gold salts, hydroxychloroquine, D-pencillamine, levamisol and cytotoxic agents, particularly cyclophosphamide and azathioprine. Antifolates, such as methotrexate and sulfasalazine belong in this latter group.

There is general agreement that methotrexate is the most successful of the DMARDs. Recently it has been marketed in low dose tablets under the trade name Rheumatrex by the Lederle Co. specifically for the treatment of rheumatoid arthritis.

This invention relates to the use of 10-deazaaminopterin as a chemotherapeutic agent for the treatment of auto-immune diseases such as rheumatoid arthritis in humans. 10-deazaaminopterin is a non-trivial analogue of methotrexate and has the following structure.

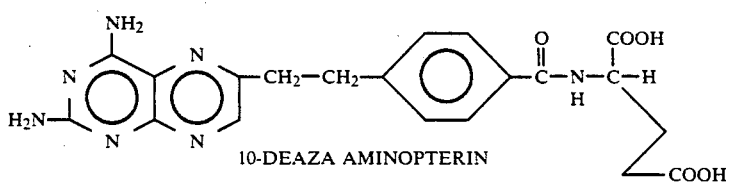

10-DEAZA AMINOPTERIN 10-deazaaminopterin differs from methotrexate with respect to the substitution at the 10th position. The N-methyl group in methotrexate is replaced by a methylene group in 10-deazaaminopterin. Methotrexate has the following structure.

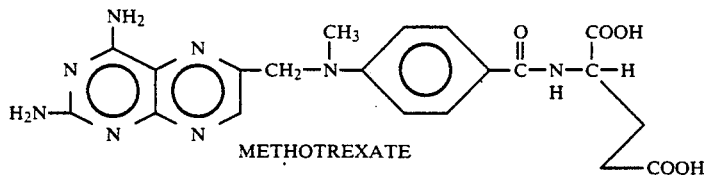

METHOTREXATE

The first synthesis of 10-deazaaminopterin was reported by DeGraw, Kisliuk, Baugh and Nair in the *Journal of Medicinal Chemistry* (17:552, 1974).

In 1982 in the *Journal of Medicinal Chemistry* (25:1227, 1982) DeGraw, Brown, Tagawa, Kisliuk, Gaumont and Sirotnak published procedures for the synthesis of a number of 10-alkyl derivatives of 10-deazaaminopterin. These 10-deazaaminopterin compounds were found to possess superior antitumor activity compared to methotrexate. Subsequently in 1983 a U.S. patent was granted to DeGraw and Sirotnak for 10-alkyl-10-deazaaminopterins for possible use as anti-cancer drugs. (U.S.

In 1985 Nair in the *Journal of Organic Chemistry* (50:1879, 1985) reported a convenient general procedure for the synthesis of both 10-deazaaminopterin and 10-alkyl-10-deazaaminopterins. Results of anticancer clinical trials with 10-deazaaminopterin established that unlike methotrexate, 10-deazaaminopterin is significantly less toxic to cancer patients. These clinical trial summaries of 10-deazaaminopterin were reported in *Cancer Treatment Reports* (71:95, 1987) by Thongprasert, Currie and Budman. According to this study, nausea and vomiting were mild, and bone marrow depression was minimal.

The target enzyme of 10-deazaaminopterin is dihydrofolate reductase. Methotrexate and 10-deazaaminopterin inhibit this enzyme to approximately the same magnitude. In 1973 Baugh, Krumdieck and Nair in *Biochemical and Biophysical Research Communication* (52:27, 1973) and Nair and Baugh the same year in the *Journal of Biochemistry* (12:3923, 1973) reported the metabolism of methotrexate to its poly-gamma-glutamates. The role of these polyglutamyl metabolites in methotrexate toxicity has now been established. In 1988 Nair, Nanvati, Kumar, Gaumont and Kisliuk reported in the *Journal of Medicinal Chemistry*, that like methotrexate 10-deazaaminopterin is also metabolized to its poly-gamma-glutamates in mammalian tissues.

Since the mechanism of action of 10-deazaaminopterin is almost identical to that of the antirheumatoid drug methotrexate, and its documented lower toxicity to humans in anticancer clinical trials, in 1988 Nair, Krumdieck, Koopman, Alarcon and Castaneda selected 10-deazaaminopterin as a potential disease modifying rheumatoid remittive drug and a clinical trial was carried out to determine its efficacy in ameliorating rheumatoid arthritis in humans.

The results of a double blind clinical trial of 10-deazaaminopterin versus methotrexate are presented in the following tables and diagrams. As expected, 10-deazaaminopterin was shown to be equally effective as methotrexate and in certain clinical parameters such as grip strength, pain and morning stiffness superior to methotrexate for the treatment of rheumatoid arthritis in humans.

10-deazaaminopterin vs Methotrexate (MTX) in Rheumatoid Arthritis (RA)

The double-blind clinical trail of 10-deazaaminopterin versus methotrexate in rheumatoid arthritis was conducted at Universidad Peruana Cayetano Heredia, Lima, Peru. In order to detect 30% differences in either direction for both -efficacy and toxicity a sample size of 20 was used. The trial was conducted according to the following protocol.

PROTOCOL

1) Objectives

The efficacy and toxicity of 10-deazaaminopterin vs methotrexate were compared in patients with RA (rheumatoid arthritis) who were eligible to receive methotrexate. The null hypotheses to be investigated included the following
1. The efficacy of 10-deazaaminopterin is equal to that of methotrexate
2. The toxicity of 10-deazaaminopterin is equal to that of methotrexate
Alternative hypotheses would be bidirectional (conceivable they could be unidirectional).
1. The efficacy of 10-deazaaminopterin is different from that of methotrexate (greater of lesser).
2. The toxicity of 10-deazaaminopterin is different from that of methotrexate (greater or lesser).

2) Subjects

Patients have failed at least 3 different nonsteroidal-anti-inflammatory drugs (NSAID)(aspirin included), and thus considered eligible for a remittive drug. They could have received (and failed) gold (oral/parenteral), d-pencillamine and/or antimalarials but they were off any of these drugs for a period of 3 months. The trial lasted 18 weeks.

3) Patient selection criteria were as follows:

Study patients were selected from those who had RA by the revised 1987 ARA criteria for no less than six months, who had the onset of RA after age 16, were between 18 and 75 years of age, and have failed (lack of efficacy or toxicity) aspirin (to tolerance), or full doses of at leas 2 different nonsteroid anti-inflammatory drugs. Patients might have failed (toxicity or lack of efficacy) a remmittive drug (oral or parenteral gold, d-pencillamine, or antimalarials), with the exclusion of methotrexate, but not necessarily had to on one. They were on an adequate method of contraception, if in their reproductive years. They had no hepatic or renal diseases (liver enzymes and creatinine were within normal limits), no thrombocytopenia (platelets $<150,000$ cells/mm$^3$), no leukopenia ($<3500$ cells/mm$^3$) and no evidence of a malignancy or an active infectious process. In addition they had six or more swollen joints and two of the following criteria: 1) nine or more joints tender on pressure, 2) 45 minutes or more of morning stiffness, 3) A Westergren erythrocyte sedimentation rate ESR of 28 min/hour or more.

The following medication restrictions were applied. Stable dose of NSAID, constant dose of prednisone not to exceed 10 mg of Prednisone (or equivalent)(stable for at least one month prior to study), no more than one intra-articular corticosteroid injection (this joint however would not be evaluated). Oxyphenylbutazone and phenylbutazone cannot be used; drugs used in the treatment of other chronic conditions (e.g. hypertension) would be allowed, but every effort was be made to maintain them at a constant dose. Acetaminophen, Codeine or proproxyphene could be used during the trial for analgesia.

4) Study design

This study was an 18 week randomized double-blind trial of 10-deazaaminopterin vs methotrexate for the treatment of RA. Randomization was performed before the study began; an equal number of patients in each arm of the protocol was secured. Codes were made available to the investigator in sealed envelopes at the beginning of the trial; they were allowed to be opened by the investigator, only if felt to be mandatory for patient management. Patients received a three week supply of either 10-deazaaminopterin or methotrexate. Both 10-deazaaminopterin and methotrexate were given in physically indistinguishable 2.5 mg capsules. Initially the patients received three capsules/week (or 7.5 mg). The capsules were taken at 12 hour intervals over a 24 hour period (8 a.m.–8 p.m. –8 a.m. the following day).

5) Evaluation

A data base which included a complete history, physical and laboratory exams was completed (Visit 0 or eligibility visit). After this visit was completed and before enrolling in the trial, patients received folic acid (1 mg/day/7 days) in order to bring all patients folate to normal or above normal values and thus avoid toxicity to either 10-deazaaminopterin or methotrexate which could conceivably be worse in those patients who were folate deficient. If the patient was felt to be eligible, he/she was entered into the trial the following week (Visit 1) at which time disease activity was assessed and a functional test completed. Patients returned to the clinic every three weeks at which time joint counts were performed, side effects monitored and laboratory studies obtained. An assessment of response was done at week nine (Visit 3). At week 18 (Visit 6) or before (if the patient decides to be removed from the trial) the patient would have a complete exit evaluation, similar to the one performed on visit 1.

Assessment included:

Patients self assessment—scale of 1–5

Morning stiffness, in minutes on the day proceding the clinic visit.

Physician's assessment—scale of 1–5

Joint counts for pain/tenderness in 60 diarthrodial joints and for swelling in 58 diarthrodial joints Laboratory tests included: CBC, with platelets and differential, Creatinine, SGOT and Alkaline phosphatase. Additionally the patients had a Westergren ESR at baseline and at completion and a chest radiograph at baseline. 5 ml of sera were secured at entry and at study completion and stored at $-20°$ C. for further studies.

Adverse effects were determined by interviewing the patient; each new symptom developing since the previous visit were recorded as to the date or onset, date of cessation, and whether it was felt to be related or unrelated to the study drug(s).

Minor itching and skin rashes could be handled with antihistaminics or topical steroids; a drop in the WBC ($<300/mm^3$) or in the platelets ($<100,000/mm^3$), or an increase in the liver enzymes $\times 2$ normal), or an increase in the baseline creatinine ($\times 2$ normal) would prompt holding the drug for one week; if the values improved, patients may be restarted on the drug; if no improvement occurs in 3 weeks, the patient should be withdrawn. Likewise, any new symptom which could conceivably be due to these drugs would prompt holding the drug until the symptom had either disappeared or improved significantly. If no improvement occurs in 3 weeks, the patient should be withdrawn from the trial. If a patient develops a serious intercurrent infectious process, or requires elective or emergency surgery during the study period, the patient should be withdrawn from the trial.

either as a first or second line remittive drug in Lima, Peru.

| (8) TIMETABLE | 0 | 1 | 3 | 4 | 5 | 6 or W/D |
|---|---|---|---|---|---|---|
| History + Physical | X | | | | | |
| Joint Evaluation | X | X | X | X | X | X |
| Chest X-ray | X | | | | | X |
| Hand/wrist films | X | | | | | |
| Sera | | X | | | | X |
| Labs | X | X | X | X | X | X |
| ESR | X | | | | | X |
| RF | X | | | | | X |
| Adverse reaction Check List | | X | X | X | X | X |
| Functional test form | | X | | | | X |
| Administration of folic acid | X | | | | | |

| 10-Deazaaminopterin vs Methotrexate in Rheumatoid Arthritis May 1989 Features of RA Patients ||
|---|---|
| Age (mean, years) | 46.8 |
| Sex (% F) | 100.0 |
| Race (% Mestizo) | 100.0 |
| Functional Class (mean) | 2.1 |
| Disease Severity | 2.2 |
| Duration of disease (mean, years) (Range 1-14) | 4.6 |

| 10-Deazaaminopterin vs Methotrexate in Rheumatoid Arthritis Toxicity Evaluation* |||
|---|---|---|
| Toxicity | 10-Deazaaminopterin | Methotrexate |
| | n = 7 | n = 7 |
| Gastrointestinal | 2 | 2 |
| Rash | 1 | 0 |
| Dizziness | 0 | 1 |
| Leukopenia | 0 | 1 |

| 10-Deazaaminopterin vs Methotrexate in Rheumatoid Arthritis Efficacy Evaluation |||||||
|---|---|---|---|---|---|---|
| | 10-Deazaaminopterin ||| Methotrexate |||
| | $V_0$ | $V_3$ | $V_6$ | $V_0$ | $V_3$ | $V_6$ |
| Features | n = 7 | n = 7 | n = 5 | n = 7 | = 7 | n = 6 |
| Joint Pain/Tenderness | 30.1 | 18.5 | 10.8 | 33.2 | 17.2 | 12 |
| Joint Swelling* | | | | | | |
| Grip Strength (mm Hg) | 21.5 | 15.2 | 11.4 | 27.8 | 23 | 13.8 |
| R | 122 | 171 | 184 | 140 | 147 | 163 |
| L | 123 | 136 | 188 | 132 | 138 | 145 |
| Morning Stiffness (h) | 1.47 | 0.60 | 0.05 | 0.84 | 0.32 | 0.37 |
| General Activity Level (0–16) | 7.8 | — | 2.2 | 6.8 | — | 3.5 |
| Pain Level (0–3) | 1.8 | — | 0.8 | 2.3 | — | 1 |
| Patient Assessment (1–5) | 2.7 | — | 2.3 | 2.3 | — | 2.1 |
| Physician Assessment (1–5) | 2.7 | — | 2.3 | 2.1 | — | 2.1 |

*60 joints for Pain/Swelling (0–3/joint), 58 joints for swelling (0–3/joint)
$V_3$ = 3rd visit
$V_6$ = 6th Visit 6) Human Subjects The study was conducted with approval of the Institutional Review Board at UPCH, Lima, Peru. Confidentiality was secured since data will be presented only in an aggregated fashion. The risks involved were the same (or maybe less) as those of taking methotrexate. Methotrexate is currently used on the treatment of RA, The results established that 10-deazaaminopterin is at least equally effective in all respects to methotrexate in the treatment of rheumatoid arthritis, and clearly superior to methotrexate in controlling pain, joint stiffness and in improving grip strength. Combined with the low frequency of toxicity and unexpectedly high attrition rate make 10-deazaaminopter n a superior drug than methotrexate in the treatment of rheumatoid arthritis in humans.

In accordance with the foregoing disclosure it has been determined that rheumatoid arthritis can be ameliorated in humans by the administration of 10-deazaaminopterin.

10-deazaaminopterin can be administered in humans by an available route including oral and parenteral. A dosage of 0.01 m to 10 mg per day in humans should be sufficient to ameliorate rheumatoid arthritis. For ease of administration 10-deazaaminopterin can be provided in composition form or preferably dosage unit form. 10-deazaaminopterin can be administered in conjunction with a carrier or diluent which can be enclosed or encapsulated in a capsule, or take the form of tablets.

Having regard to the foregoing disclosure, the following is claimed as inventive and patentable embodiments of thereof:

1. A process for treating rheumatoid arthritis, which comprises administering to humans having rheumatoid arthritis, a therapeutic and relatively nontoxic amount of 10-deazaaminopterin to ameliorate rheumatoid arthritis.

2. The process according to claim 1 wherein the dosage to be administered comprises an amount within the range from 0.1 to about 100 mg of 10-deazaaminopterin.

3. A process according to claim 1 in which the 10-deazaaminopterin is administered orally or parenterally.

* * * * *